United States Patent [19]

McAleer et al.

[11] Patent Number: 5,024,836

[45] Date of Patent: Jun. 18, 1991

[54] STABLE LYOPHILIZED LIVE HERPES VIRUS VACCINE

[75] Inventors: William J. McAleer, Avalon, N.J.; Robert Z. Maigetter, Mechanicsville; Henry Z. Markus, Wyncote, both of Pa.

[73] Assignee: Merck & Co., Inc., Rahway, N.J.

[21] Appl. No.: 423,658

[22] Filed: Oct. 19, 1989

Related U.S. Application Data

[63] Continuation of Ser. No. 183,530, Apr. 14, 1988, abandoned, which is a continuation-in-part of Ser. No. 45,940, May 4, 1987, abandoned.

[51] Int. Cl.$^5$ .................... A61K 39/12; C12N 7/00
[52] U.S. Cl. .................... 424/89; 435/235.1; 435/236; 435/237; 435/238
[58] Field of Search .................. 424/89; 435/235-238

[56] References Cited

U.S. PATENT DOCUMENTS

| | | | |
|---|---|---|---|
| 3,961,046 | 6/1976 | Cerini | 424/89 |
| 4,000,256 | 12/1976 | Hilleman et al. | 424/89 |
| 4,273,762 | 6/1981 | McAleer et al. | 424/89 |
| 4,324,861 | 4/1982 | Kan | 435/237 |
| 4,337,242 | 6/1982 | Markus et al. | 424/89 |
| 4,351,827 | 9/1982 | Bijlenga | 424/89 |
| 4,622,222 | 11/1986 | Horváth et al. | 424/89 |

OTHER PUBLICATIONS

Phillips et al., "A Study of Water Binding in Lyophilized Viral Vaccine Systems", Chemical Abstracts, p. 368, vol. 95, Ref. #138440m, 1981.

Phillips et al., "A Study of Water Binding in Lyophilized Viral Systems", Cryobiology, vol. 18, No. 4, pp. 414–419, 1981.

Biological Abstract 83014029.

*Primary Examiner*—Margaret Moskowitz
*Assistant Examiner*—Abdel A. Mohamed
*Attorney, Agent, or Firm*—Donald J. Perrella; Roy D. Meredith; Charles M. Caruso

[57] ABSTRACT

The invention comprises a lyophilized live herpes virus vaccine that comprises from about 0.5% to about 8% moisture.

8 Claims, No Drawings

STABLE LYOPHILIZED LIVE HERPES VIRUS VACCINE

RELATED APPLICATION

This is a continuation of application Ser. No. 183,530, filed Apr. 14, 1989, abandoned, which is a continuation-in-part of Ser. No. 07/045,940, filed May 4, 1987, also abandoned.

BACKGROUND OF THE INVENTION

Herpes viruses are a large group of intranuclear, double-stranded DNA viruses that are remarkably cagable of establishing a latent infection many years after a primary infection. The herpes virus group is responsible for such diseases as fever blister and keratoconjunctivitis (Herpes simplex virus type 1), venereal disease (Herpes simplex virus type 1 and 2), chickenpox (varicella) and shingles (Herpes zoster), cytomegalic inclusion disease (Cytomegalovirus), Marek's disease of chickens and infectious mononucleosis (Epstein-Barr virus).

Chickenpox (varicella) is one of the most common and highly communicable diseases and occurs primarily in childhood. A rash is observed generally over the entire body together with an attack of fever which occurs after an incubation period generally running between 14 and 17 days. The disease results in a mucular rash which may, in many cases, form pustules and, in extreme cases, leave scars. Other problems and complications may arise, for instance, in the case of undernourished children who may have necrotic dermal ulcer. Other complications such as central nervous system disturbance, myelitis and neuritis were known to occur as results from chickenpox.

A live varicella vaccine is known. U.S. Pat. No. 3,985,615, the disclosure of which is incorporated herein by reference, discloses a process for making a live varicella vaccine which comprises passaging the varicella virus in a guinea pig primary embryonic tissue cell at a temperature of from 32° C. to 37° C. until the virus is adequately attenuated.

Aqueous solutions of live virus vaccines are known to be unstable during storage. The conventional technique to reduce storage instability is to remove moisture by lyophilization. Conventional wisdom holds that the more moisture that is removed, the higher the storage stability of the live virus vaccine. Generally, live virus vaccines are lyophilized to moisture levels of less than about 1%.

Surprisingly, it has now been discovered that lyophilizing a live herpes virus vaccine to result in a moisture content within the range of from about 0.5% to about 8% results in increased storage stability to the live herpes virus vaccine. The increased storage stability permits the live herpes virus vaccine to be stored at 5° C., i.e. in a refrigerator, rather than at $-20°$ C., i.e. in a freezer.

SUMMARY OF THE INVENTION

The invention comprises a lyophilized live herpes virus vaccine that comprises from about 0.5% to about 8% moisture. Another aspect of the invention relates to a lyophilized tetravalent measles, mumps, rubella and varicella vaccine.

DETAILED DESCRIPTION OF THE INVENTION

The invention comprises a lyophilized live herpes virus vaccine that comprises from about 0.5% to about 8% moisture. Within the foregoing range, useful subsets are from about 0.5% to about 2%, from about 2% to about 5%, and from about 5% to about 8%. Surprisingly, such levels of moisture result in increased storage stability of the live herpes virus vaccine. This enhanced stability permits the vaccine to be stored at 5° C., i.e. standard refrigerator conditions while maintaining stability, rather than at $-20°$ C., freezer conditions.

It is believed that the storage stability of any live herpes virus vaccine can be enhanced. A preferred live herpes virus vaccine is varicella. A live varicella vaccine can be produced by the technique described in U.S. Pat. No. 3,985,615.

The live herpes virus vaccine can then be lyophilized to a moisture content of from about 0.5% to about 8%. Standard lyophilization techniques can be utilized. However, it has been observed that by utilizing gas injection, e.g. sterile argon, during the primary cycle of the lyophilization process that the desired product temperature, which characterizes the completion of the primary cycle, is obtained in a compacted time period, e.g. as short as about five hours rather than about 40 hours.

Another advantage of the invention is that the lyophilization time required to achieve the moisture levels of the invention is much less than the lyophilization time to achieve moisture levels below 0.5%. This is due to the fact that the secondary cycle of the lyophilization process controls the resulting moisture content of the live herpes virus vaccine. To achieve the moisture content of the invention requires a shorter secondary cycle than to achieve moisture levels below 0.5%. To achieve the preferred moisture content of the invention the secondary can be carried out for about three to about five hours.

Accordingly, in another aspect of the invention there is a lyophilization process for a live herpes virus vaccine which comprises a primary cycle with gas injection and a secondary cycle wherein the time of the primary cycle plus the secondary cycle is for about 7 hours to about 11 hours.

Another aspect of the invention relates to a lyophilized tetravalent vaccine comprising at least about 20, preferably at least about 1,000 $TCID_{50}$ units of measles vaccine, at least about 317, preferably at least about 5,000 $TCID_{50}$ units of mumps vaccine, at least about 40, preferably at least about 1,000 $TCID_{50}$ units of rubella vaccine and at least about 53, preferably at least about 1,000 pfu of varicella vaccine per dose. Such tetravalent vaccine is efficacious against all four viruses; there is little interference.

The following examples illustrate the invention without, however, limiting the same thereto.

EXAMPLE I

Approximately 100 vials live virus varicella vaccine were prepared in accordance with the method outlined in U.S. Pat. No. 3,985,615 and were then frozen using liquid nitrogen.

The 100 vials which were unsealed but covered with a two position rubber stopper, were placed on a precooled lyophilizer shelf (a Usifroid lyophilizer) with a starting shelf temperature of $-45°$ C. For the primary cycle, the vials were heated from −45° C. to 30° C. over an 8 hour period. The shelf temperature heat-up rate was 9.4° C./hour. The pressure control for the primary cycle was 0.10 to 0.18 mbar. (at 75 to 150 microns), which was controlled by injecting dry, sterile argon. After the primary cycle, gas injection was shut off and full vacuum was applied. The secondary cycle was then carried out for 9 hours at 30° C., resulting in a final shelf temperature of 30° C.

The pressure in the chamber was raised, with dry, sterile argon, to about 0.2 to about 0.27 bars. The vials were then sealed with the rubber stopper covering each vial and the chamber pressure was now brought to atmospheric pressure with dry sterile argon.

The chamber was then opened, the vials removed and each vial capped with an aluminum seal.

The moisture content of the final product, which was determined by the Dupont Aqua Test ™, was 2.2%. This was Batch I.

The above procedure was repeated for a second batch (BATCH II), but during the primary cycle the shelf temperature heat-up rate was 21.4° C./hour for 3.5 hours, the pressure control was 0 45 to 0.5 mbar and the secondary cycle was for four hours. The moisture content for this batch was 7.7%. This same procedure was repeated for a third batch (BATCH III), and the resulting moisture content was 6.4%. For these studies, the three batches were compared to a control which was prepared by conventional lyophilization where the primary cycle was 40 hours and the secondary cycle was 8 hours; the total cycle time was approximately 56 hours. The primary drying was performed at −28° C. for 40 hours at $1.3 \times 10^{-3}$ mbar (1 micron); the secondary cycle was held at +26° C. The time interval between the primary and secondary cycle was about 8 hours with a 6.75° C./hour rise in temperature during that time. The moisture content for this batch was 0.6%.

The batches were stored at 5° C. The storage stability of the live virus varicella vaccine was determined by the number of plague forming units (PFU) as determined by the plague assay.

The estimated half-life is presented in the following table:

Estimate Half-Life at 2°−8° C. for Air Injection Lots of Varicella Virus Vaccine

| Lot | Lyophilization | Percent Moisture | Estimated Half-Life (Months) |
|---|---|---|---|
| BATCH I | GI | 2.2% | 4.6 |
| BATCH II | GI | 7.7% | 5.8 |
| BATCH III | GI | 6.4% | 6.4 |
| CONTROL | | 0.6% | 1.6 |

GI = gas injection lyophilization, control = 48-hour cycle, no gas injection.

Thus, one can see that over time that higher moisture lots are more stable than lower moisture control lots.

EXAMPLE II

Preparation of Combined MMRV Vaccine

Frozen samples of Measles, Mumps, Rubella and Varicella vaccines were thawed in a warm water bath (30° C.).

Measles Component 100 ml of Measles Vaccine, Edmondston, More Attenuated Strain with an infectivity titer of 4.95 $\log_{10}$ $TCID_{50}/0.1$ ml was used.

Mumps Component 500 ml of Mumps Vaccine, Jerryl Lynn Strain (U.S. Pat. No. 3,555,149) with an infectivity titer of 5.4 $\log_{10}$ $TCID_{50}/0.1$ ml was used.

Rubella Component 100 ml of Rubella Vaccine; RA 27/3 Strain Wistar, with an infectivity titer of 4.65 $\log_{10} TCID_{50}/0.1$ ml was used.

Varicella Component 150 ml of Varicella Vaccine, Oka Strain, with an infectivity titer of 320,000 PFU/ml.

After thawing, the components were pooled in a sterile 4 L bottle. To the 850 ml virus pool were added the following diluents:

50 ml—Minimum Essential Medium 0.0565%, Sorbitol 4.291%, Gelatin 4.985%, Sodium Bicarbonate 0.354%, Albumin 2.4%.

525 ml—Modified Gelatin, Medium O, Sorbitol Diluent containing: Medium 199 6.82%, Sorbitol 3.9725%; Gelatin 3.9725%, Sodium Bicarbonate, 0.225%.

225 ml—1 Molar Phosphate Buffer Solution (Dibasic Potassium Phosphate 5.72%; Monobasic Potassium Phosphate 8.239%).

1350 ml—SPGA/(Sucrose 7.46%; Dibasic Potassium Phosphate 0.135%. Monobasic Potassium Phosphate 0.045%, Monosodium Glutamate 0.0956%, Albumin 10%).

The mixture of virus and diluents was mixed by swirling at room temperature. The mixture was then held at 4° C. in an ice bath for filling and lyophilization.

The combined MMRV vaccine was filled in 0.7 ml units into glass vials. The filled vials were frozen by liquid nitrogen and lyophilized to approximately 1% moisture. After lyophilization the vials were stoppered and sealed with aluminum seals, and stored at −20° C.

Lyophilized samples were submitted for infectivity assay according to standard assay procedures. Final assay results:

Measles=3.3 $\text{Log}_{10}$ $TCID_{50}/0.1$ ml=2,000 $TCID_{50}/0.1$ ml,
Mumps=4.2 $\text{Log}_{10}$ $TCID_{50}/0.1$ ml=16,000 $TCID_{50}/0.1$ ml
Rubella=3.1 $\text{Log}_{10}$ $TCID_{50}/0.1$ ml=16,000 $TCID_{50}/0.1$ ml
Varicella=5170 PFU/ml.

EXAMPLE III

Approximately 50 vials of MMRV vaccine was pared as described in Example II, but were lyophilized as follows:

The vials which were unsealed but covered with a two position, rubber stopper, were placed on a pre-cooled lyophilizer shelf (a Usifroid lyophilizer) with a starting shelf temperature of −45° C. For the primary cycle and secondary cycle as well as all other parameters, the lyophilizer was run using conditions similar to those described for BATCH II and III of the Varicella virus alone; i.e. Example I, which is denoted BATCH IV.

When the vials were tested for potency for measles, mumps, rubella and varicella, it was clear that gas injection samples had potency similar to those samples that were lyophilized without gas-injection (i.e. lower moisture). See Example II.

The results were as follows:

MMRV Potency Assay on Gas-Injection Vaccine

| BATCH | Varicella (PFU/ml) | Mumps (TCID$_{50}$/0.1 ml) | Rubella (TCID$_{50}$/0.1 ml) | Measles (TCID$_{50}$/0.1 ml) | Moisture |
|---|---|---|---|---|---|
| BATCH IV | 4.89 | 3.9 | 3.2 | 3.4 | 3.36 |

What is claimed is:

1. A gas injected lyophilized live attenuated varicella virus vaccine which comprises 2% to 8% moisture.

2. The lyophilized live attenuated varicella virus vaccine of claim 1 wherein said moisture content is 2.0 to 2%.

3. The lyophilized live attenuated varicella virus vaccine of claim 1 wherein said moisture content is 2% to 5%.

4. The lyophilized live attenuated varicella virus vaccine of claim 1 wherein said moisture content is 5% to 8%.

5. A lyophilized live attenuated varicella virus vaccine which is combined with a measles vaccine, mumps vaccine, rubella vaccine to form a tetravalent lyophilized vaccine having a moisture content of from 2% to 8% wherein each of said vaccines is present in an immunologically effective amount that is effective to immunize a recipient against each of said viruses.

6. The vaccine of claim 5 wherein the lyophilized vaccine comprises 2% moisture.

7. The vaccine of claim 5 wherein the lyophilized vaccine comprises 2% to 5% moisture.

8. The vaccine of claim 5 wherein the lyophilized vaccine comprises 5% to 8% moisture.

* * * * *